US009989487B2

(12) United States Patent
Mizutani et al.

(10) Patent No.: US 9,989,487 B2
(45) Date of Patent: Jun. 5, 2018

(54) GAS SENSOR

(71) Applicant: NGK Spark Plug Co, LTD., Nagoya (JP)

(72) Inventors: Masaki Mizutani, Niwa-gun (JP); Yuta Oishi, Niwa-gun (JP); Masaki Onkawa, Konan (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 450 days.

(21) Appl. No.: 14/709,970

(22) Filed: May 12, 2015

(65) Prior Publication Data

US 2015/0323492 A1    Nov. 12, 2015

(30) Foreign Application Priority Data

May 12, 2014  (JP) ................................ 2014-098705
Apr. 7, 2015   (JP) ................................ 2015-078655

(51) Int. Cl.
*G01N 27/407*   (2006.01)
*G01N 27/406*   (2006.01)

(52) U.S. Cl.
CPC ..... *G01N 27/4062* (2013.01); *G01N 27/4071* (2013.01)

(58) Field of Classification Search
CPC ........... G01N 27/4062; G01N 27/4071; G01N 27/407–27/41
See application file for complete search history.

(56) References Cited

U.S. PATENT DOCUMENTS

| | | | | |
|---|---|---|---|---|
| 6,562,215 B1* | 5/2003 | Nelson | ............... | G01N 27/4071 204/421 |
| 2001/0047939 A1* | 12/2001 | Springhorn | ........ | G01N 27/4071 204/431 |
| 2008/0016942 A1* | 1/2008 | Mizutani | ............ | G01N 27/4071 73/23.2 |

FOREIGN PATENT DOCUMENTS

JP    4093784 B    10/2003

* cited by examiner

*Primary Examiner* — J. Christopher Ball
(74) *Attorney, Agent, or Firm* — Leason Ellis LLP (57) ABSTRACT

A gas sensor element of an air/fuel ratio sensor includes a plurality of through holes formed in an insulating substrate at forward end regions of corresponding electrode pads to which the through holes are connected. In the gas sensor element, the through holes are not formed within the longitudinal rear end regions and center regions of the electrode pads. Since in each of the electrode pads, the region of the electrode pad other than its forward end region occupies a greater area than that of the forward end region, it is easy to bring connection terminals into contact with the regions of the electrode pads other than their forward end regions. Therefore, it is possible to prevent the connection terminals from coming into contact with the through holes, so as to thereby prevent occurrence of an electrical connection failure between the connection terminals and the electrode pads.

18 Claims, 8 Drawing Sheets

GAS SENSOR

This application claims the benefit of Japanese Patent Applications No. 2014-098705, filed May 12, 2014 and No. 2015-078655, filed Apr. 7, 2015, all of which are incorporated by reference in their entities herein.

FIELD OF THE INVENTION

The present invention relates to a gas sensor including a cell having a solid electrolyte body and a pair of electrodes, a plate-shaped insulating substrate laminated on the cell, and a plurality of electrode pads disposed on an outer surface of the insulating substrate.

BACKGROUND OF THE INVENTION

An example of a gas sensor for detecting a particular gas component contained in gas to be measured is a gas sensor having a longitudinally extending plate-shaped cell for generating a sensor signal in accordance with the particular gas component; an insulating substrate which is formed of a plate-shaped insulating material laminated on the cell and which has a plurality of through holes in a rear end region thereof, which through holes extend through the insulating substrate in its thickness direction and have conductors disposed therein; and a plurality of electrode pads disposed on an outer surface of the insulating substrate and electrically connected to the cell through the plurality of through holes (more specifically, the conductors disposed therein) for outputting the sensor signal to the outside of the sensor.

An example of such a conventional cell is an embedded-type cell which includes a frame member formed of a longitudinally extending plate-shaped insulating material and having a hollow space in a forward end region thereof, a solid electrolyte body disposed within the hollow space, a pair of electrodes formed on outer surfaces of the solid electrolyte body; a pair of longitudinally extending leads connected to the electrodes (Japanese Patent No. 4093784).

Adoption of such an embedded-type cell reduces the amount of the solid electrolyte body used in the cell, thereby reducing manufacturing costs of the gas sensor.

Another gas sensor for detecting a particular gas component contained in gas to be measured includes, in addition to all the above-described elements of the conventional gas sensor, a plurality of connection terminals connected to the electrode pads, and a metallic shell for holding the gas sensor element in a state in which the connection terminals are connected to the electrode pads (Japanese Patent No. 4093784).

Problem to be Solved by the Invention

However, the above-described conventional gas sensor may fail to properly output the sensor signal when an electrical connection failure occurs between the electrode pads and the connection terminals.

For example, in the case where the plurality of through holes are formed in the insulating substrate at different longitudinal positions, any of the plurality of electrode pads may come into contact with a corresponding connection terminal at a position where a through hole is formed. Examples of the configuration of the conductor disposed within a through hole include one in which a conductor is disposed along the inner wall surface of a through hole such that a hollow space remains along the center axis (the penetration direction) of the through hole, and another one in which a conductor fills a through hole.

In the case of through holes which employ the configuration in which a conductor is disposed in each through hole such that a hollow space remains along the center axis, the following problem may arise. Specifically, if any one of the plurality of connection terminals comes into contact with a corresponding electrode pad at a position where a through hole is formed, the area of contact between the connection terminal and the electrode pad becomes smaller, possibly causing an electrical connection failure between the electrode pad and the connection terminal.

Not only in the case of through holes which employ the configuration in which a conductor is disposed in each through hole such that a hollow space remains along the center axis, but also in the case of through holes which employ the configuration in which each through hole is filled with a conductor, some connection terminals may be deformed in a step of assembling the gas sensor element and the connection terminals. Specifically, when the connection terminals are moved (slid) on the outer surface of the gas sensor element from the rear end side toward the forward end side thereof in the step of assembling the gas sensor element and the connection terminals, some connection terminals may be caught by the through holes and deformed. When such deformation of the connection terminals occurs, there arises the possibility that an electrical connection failure occurs between the connection terminals and the electrode pads (wire breakage anomaly).

In view of the foregoing problem, an object of the present invention is to provide a gas sensor which can restrain occurrence of an electrical connection failure between connection terminals and electrode pads.

SUMMARY OF THE INVENTION

Means for Solving the Problem

A gas sensor according to one aspect of the present invention includes a gas sensor element, a plurality of connection terminals, and a metallic shell, and detects a particular gas component contained in gas to be measured.

The gas sensor element includes a cell, an insulating substrate, and a plurality of electrode pads.

The cell includes a frame member, a solid electrolyte body, a pair of electrodes, and a pair of leads.

The frame member is formed of a plate-shaped insulating material extending in a longitudinal direction of the gas sensor element, and has a hollow space in a forward end region thereof and a plurality of first through holes in a rear end region thereof which extend through the frame member in a thickness direction thereof and each of which has a conductor disposed therein. The solid electrolyte body is disposed within the hollow space. The pair of electrodes are formed on an outer surface of the solid electrolyte body. The pair of leads are connected to the electrodes and the first through holes and extend in the longitudinal direction.

The insulating substrate is formed of a plate-shaped insulating material laminated on the cell, and has in a rear end region thereof a plurality of second through holes which extend therethrough in the thickness direction, each of which has a conductor disposed therein, and which communicate with the plurality of the first through holes. The plurality of electrode pads are disposed on an outer surface of the insulating substrate and connected to the plurality of second through holes.

The plurality of connection terminals are connected to the electrode pads. The metallic shell holds the gas sensor element in a state in which the connection terminals are connected to the electrode pads.

The plurality of second through holes are formed in the insulating substrate at positions within forward end regions of the corresponding electrode pads to which the second through holes are connected.

In the thus-configured gas sensor, the second through holes are formed within the forward end regions of the electrode pads, rather than being formed within longitudinal rear end regions and center regions of the electrode pads. Since in each of the electrode pads, the region of the electrode pad other than its forward end region (i.e. its rear end region and its center region) occupies a greater area than that of the forward end region, it becomes easy to bring the connection terminals into contact with the regions of the electrode pads other than their forward end regions.

Since it becomes easy to employ a configuration in which the connection terminals are connected to the regions of the electrode pads other than their forward end regions as descried above, it is possible to restrain the connection terminals from coming into contact with the second though holes, to thereby restrain occurrence of an electrical connection failure between the connection terminals and the electrode pads.

The second through holes are formed within the forward end regions of the electrode pads. This configuration prevents the connection terminals from moving over the second through holes when the connection terminals are moved (slid) on the outer surface of the gas sensor element from the rear end side toward the forward end side thereof in a step of assembling the gas sensor element and the connection terminals which are to be connected to the electrode pads. As a result, it is possible to restrain some of the connection terminals from being caught by the second through holes and deformed. Thus, it is possible to restrain occurrence of an electrical connection failure between the connection terminals and the electrode pads (wire breakage anomaly) due to the deformation of the connection terminals.

Therefore, the gas sensor element according to the present invention can restrain occurrence of an electrical connection failure between the electrode pads and the connection terminals.

Notably, the configuration in which the second through holes are formed within the forward end regions of the electrode pads can decrease the length of the leads of the cell compared to the configuration in which the second through holes are formed within the rear end regions of the electrode pads. Therefore, the former configuration reduces the amount of noble metal used for the leads, thereby reducing manufacturing costs of the gas sensor.

Furthermore, examples of the configuration of the conductor disposed in each of the first through holes and the second through holes include one in which a conductor is disposed along the inner wall surface of a through hole such that a hollow space remains along the center axis (the penetration direction) of the through hole, and another one in which a conductor fills a through hole.

In the gas sensor of the present invention, the plurality of electrode pads may be disposed such that a gap in a width direction of a face of the insulating substrate is formed between the plurality of electrode pads.

In this case, an electrical connection failure (short-circuit anomaly) due to electrical continuity between the electrode pads becomes less likely to occur. Specifically, when the connection terminals are moved (slid) on the outer surface of the gas sensor element from the rear end side toward the forward end side thereof in the step of assembling the gas sensor element and the connection terminals, the electrode pads may be scraped by the connection terminals and shavings (pieces of the scraped material) of the electrode pads may be produced. Even in such a case, an electrical connection failure (short-circuit anomaly) due to electrical continuity between the electrode pads is less likely to occur.

More specifically, when shavings of the electrode pads are produced, the shavings move mainly in the longitudinal direction of the face of the insulating substrate which is the direction in which the connection terminals move, and the range of the movement of the shavings in the width direction of the face of the insulating substrate (i.e., in the transverse direction) is small. Since the plurality of electrode pads are disposed such that a widthwise gap is formed between the electrode pads, electrical continuity between the electrode pads due to shavings becomes less likely to occur.

Therefore, the gas sensor element of the present invention can restrain occurrence of an electrical connection failure between the electrode pads and the connection terminals.

In the gas sensor of the present invention, the plurality of electrode pads may be disposed such that a gap in the longitudinal direction of the face of the insulating substrate is formed between the plurality of electrode pads.

As a result of the plurality of electrode pads being disposed such that a lengthwise gap is formed between the electrode pads, the plurality of electrode pads are disposed apart from one another by a sufficient distance. Therefore, an electrical connection failure (short-circuit anomaly) due to electrical continuity between the electrode pads caused by any foreign matter becomes less likely to occur.

In the case where the plurality of electrode pads are disposed such that the widthwise gap and the lengthwise gap are formed between the electrode pads, an electrical connection failure (short-circuit anomaly) due to electrical continuity between the electrode pads becomes more likely to occur.

Therefore, in the gas sensor of the present invention, an electrical connection failure (short-circuit anomaly) due to electrical continuity between the plurality of electrode pads becomes less likely to occur.

Next, in the gas sensor according to the present invention, the distance between the first through holes may be 2.3 [mm] or less.

As a result of the plurality of first through holes being arranged such that the distance between the first through holes falls within such a numerical value range, the region where the first through holes are formed can be reduced in size, and the gas sensor element can be reduced in size.

Since the cell of the gas sensor according to the present invention is an embedded-type cell in which a solid electrolyte body is disposed within a hollow space of a frame member, the first through holes can be formed in the frame member formed of an insulating material, rather than in the solid electrolyte body. As a result, even in the case where the distance between the plurality of first through holes is rendered less than 4.8 [mm], occurrence of leak current (leakage current) between the plurality of first through holes can be restrained.

Therefore, according to the present invention, it is possible to restrain occurrence of leak current (leakage current) between the plurality of first through holes and to restrain occurrence of an anomaly in current paths extending from the electrodes of the cell to the electrode pads.

Next, in the gas sensor element according to the present invention, each of the electrode pads may have a shape determined such that the maximum width of a rear end region of the electrode pad located rearward of a center point of the corresponding second through hole is greater than the maximum width of a forward end region of the electrode pad located forward of the center point of the corresponding second through hole.

This means that, since the respective rear end regions of the electrode pads located rearward of the center points of the corresponding through holes serve as contact regions for contact with the connection terminals, the electrode pads whose rear end regions have larger maximum widths can achieve good electrical contact with the connection terminals.

As a result, the gas sensor of the present invention can restrain occurrence of an electrical connection failure between the electrode pads and the connection terminals.

Effect of the Invention

The gas sensor according to the present invention can restrain occurrence of an electrical connection failure between the electrode pads and the connection terminals.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

Embodiments of the present invention will next be described with reference to the drawings.

The following embodiments will be described while referring to a full range air/fuel ratio sensor (hereinafter, may be referred to as merely the air/fuel ratio sensor), which is a kind of oxygen sensor among gas sensors. Specifically, the following description will refer to an air/fuel ratio sensor which is used for air/fuel ratio feedback control in automobiles or various types of internal combustion engines. The air/fuel ratio sensor is attached to an exhaust pipe of an internal combustion engine and includes a gas sensor element (detecting element) for detecting a particular gas (oxygen) contained in gas to be measured; specifically, exhaust gas.

1. First Embodiment 1-1. Overall Configuration

Figure 1:
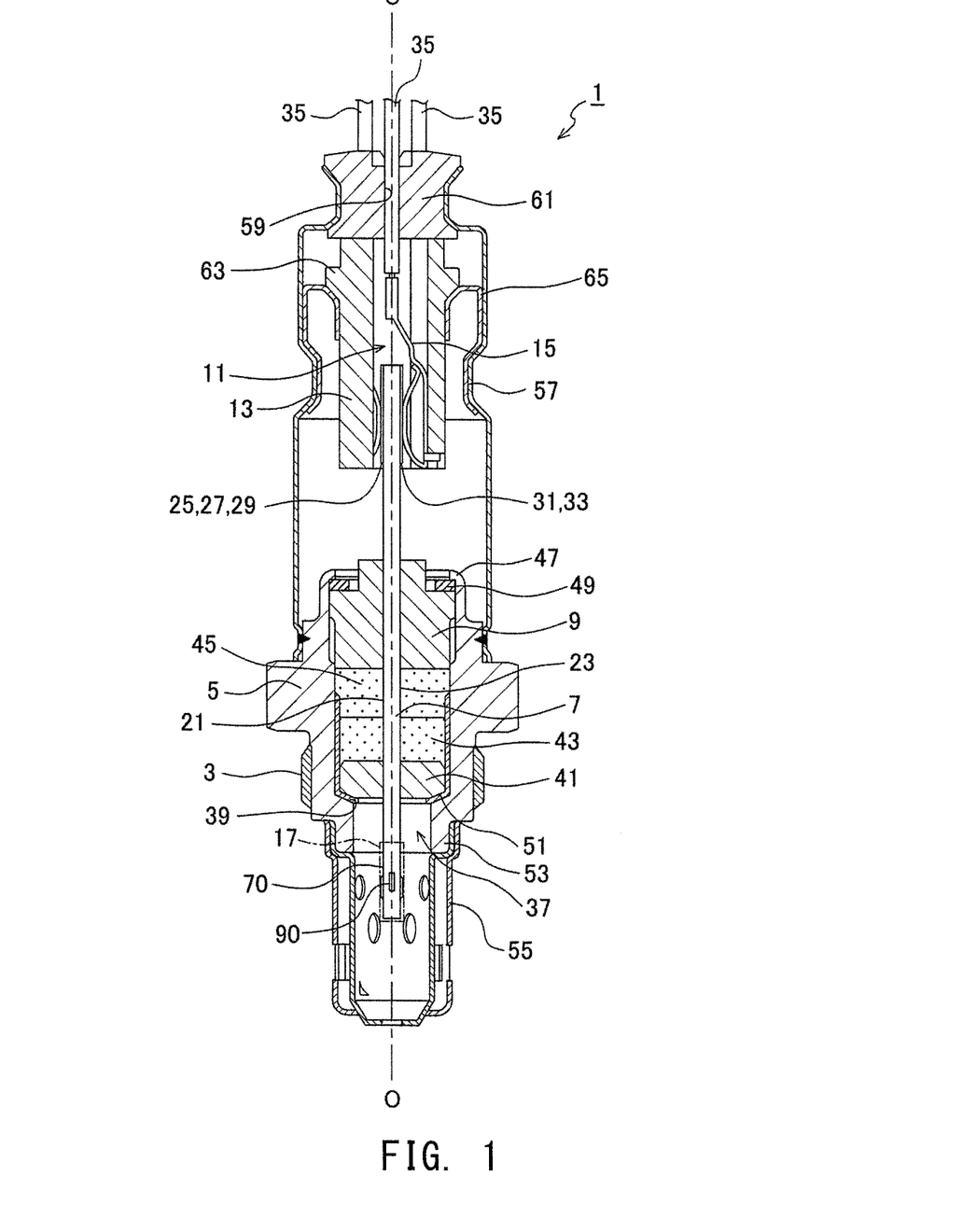
FIG. 1 is a sectional view showing the internal configuration of an air/fuel ratio sensor.

The overall configuration of an air/fuel ratio sensor which uses a gas sensor element of the present embodiment will be described with reference to FIG. 1. FIG. 1 is a sectional view showing the internal configuration of the air/fuel ratio sensor.

As shown in FIG. 1, the air/fuel ratio sensor 1 of the present embodiment includes a tubular metallic shell 5 having a threaded portion 3 formed on its outer surface and adapted to fix it to an exhaust pipe; a plate-shaped gas sensor element 7 extending in the direction of an axial line 0 (a longitudinal direction of the air/fuel ratio sensor 1, a vertical direction in FIG. 1); a tubular ceramic sleeve 9 disposed in such a manner as to radially surround the gas sensor element 7; an insulating contact member 13 (separator 13) which has an insertion hole 11 extending therethrough in the direction of the axial line 0 and which is disposed such that the inner wall surface of the insertion hole 11 surrounds a rear end portion of the gas sensor element 7; and five connection terminals 15 (FIG. 1 shows only two of them) disposed between the gas sensor element 7 and the separator 13.

As will be described in detail later, the gas sensor element 7 includes a rectangular-parallelepiped element body 70 extending in the longitudinal direction, and a porous protection layer 17 which covers a forward end portion of the element body 70. The element body 70 has a detecting section 90 provided in its forward end region and adapted to detect a particular gas contained in gas to be measured. Also, the gas sensor element 7 has electrode pads 25, 27, 29, 31, and 33 formed on the outer surface of its rear end portion (an upper end portion in FIG. 1, a longitudinally rear end portion); specifically, on a first main surface 21 and a second main surface 23 of the rear end portion, which are located on the front and back sides of the gas sensor element 7 (see FIGS. 2 and 3 for detail).

The connection terminals 15 are electrically connected to the electrode pads 25, 27, 29, 31, and 33, respectively, of the gas sensor element 7, and are also electrically connected to respective lead wires 35 extending into the sensor from outside, thereby forming electrical current paths through which electric current flows between an external device connected to the lead wires 35, and the electrode pads 25, 27, 29, 31, and 33.

The metallic shell 5 has a substantially tubular shape and is configured to have a through hole 37 extending therethrough in the direction of the axial line 0 and a ledge 39 protruding radially inward from the wall surface of the through hole 37. The metallic shell 5 holds the gas sensor element 7 inserted through the through hole 37 in such a manner that the detecting section 90 is disposed forward of the forward end of the through hole 37, while the electrode pads 25, 27, 29, 31, and 33 are disposed rearward of the rear end of the through hole 37.

Also, in the through hole 37 of the metallic shell 5, an annular ceramic holder 41, a talc ring 43, a talc ring 45, and the ceramic sleeve 9 are stacked rearward in this order in such a manner as to radially surround the gas sensor element 7.

A crimp packing 49 is disposed between the ceramic sleeve 9 and a rear end portion 47 of the metallic shell 5, while a metallic holder 51 for holding the talc ring 43 and the ceramic holder 41 is disposed between the ceramic holder 41 and the ledge 39 of the metallic shell 5. The rear end portion 47 of the metallic shell 5 is crimped in such a manner as to press forward the ceramic sleeve 9 through the crimp packing 49.

Furthermore, a protector 55 made of metal (e.g., stainless steel) and having a dual structure is attached to the outer circumference of a forward end portion 53 of the metallic shell 5 by, for example, welding and covers a protruding portion of the gas sensor element 7.

Meanwhile, an outer tube 57 is fixed to the outer circumference of a rear portion of the metallic shell 5. A grommet 61 having lead wire insertion holes 59 formed therein is disposed in a rear opening of the outer tube 57, and the five lead wires 35 (FIG. 1 shows three of them) are inserted through the respective lead wire insertion holes 59 and are electrically connected to the electrode pads 25, 27, 29, 31, and 33, respectively.

The separator 13 has a collar portion 63 formed along its outer circumference, and the collar portion 63 is fixed to the outer tube 57 through a holding member 65.

1-2. Configuration of Gas Sensor Element

Next, the configuration of the gas sensor element 7, which is an essential member of the present embodiment, will be described in detail with reference to FIGS. 2 to 5.

Figure 2:
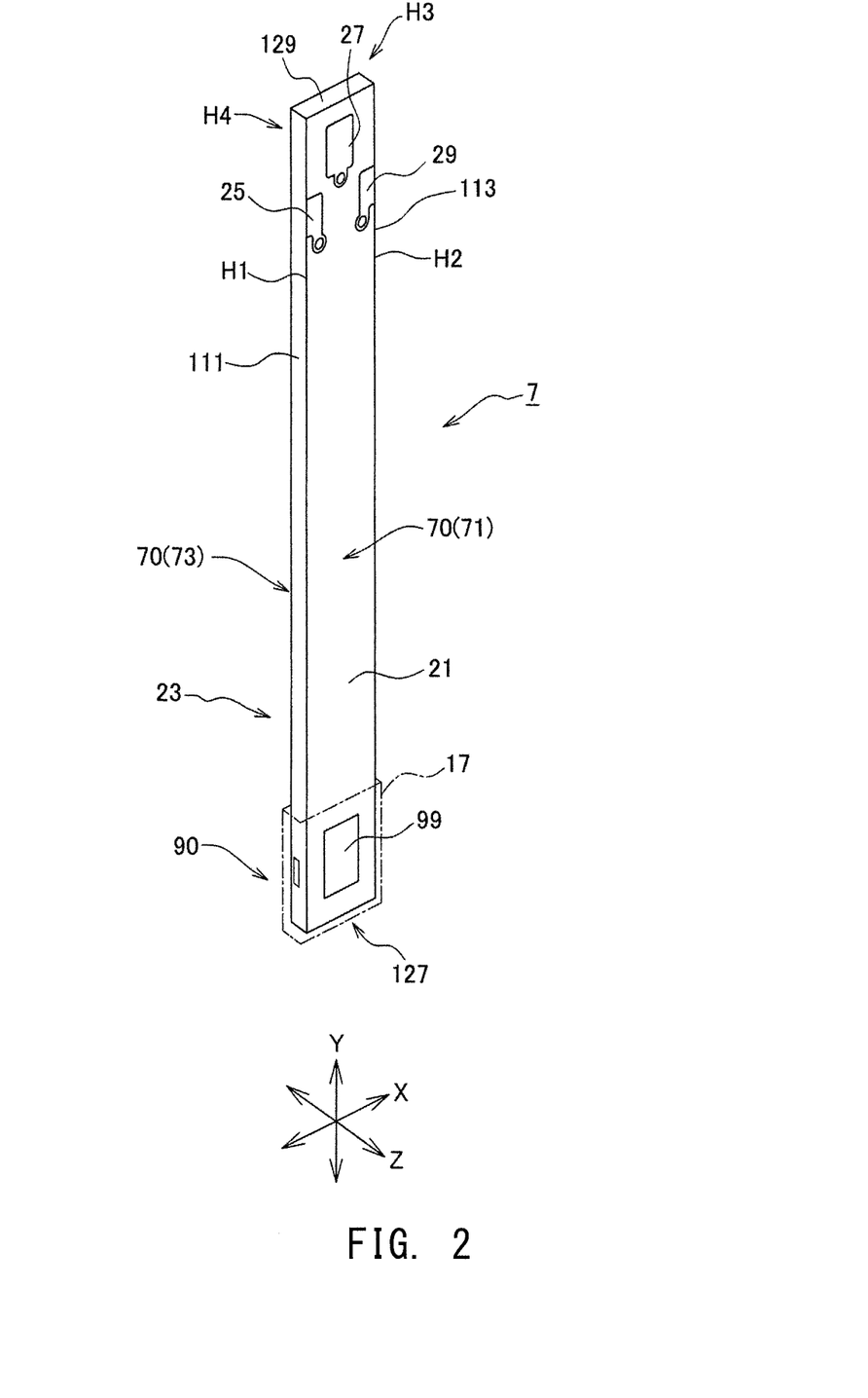
FIG. 2 is a perspective view showing the appearance of a gas sensor element.

FIG. 2 is a perspective view showing the appearance of the gas sensor element 7.

As shown in FIG. 2, the gas sensor element 7 is an elongated plate member extending in the longitudinal direction (Y-axis direction). In FIG. 2, the longitudinal direction corresponds to the direction of the axial line 0 of the gas sensor. Also, in FIG. 2, a Z-axis direction is a lamination direction perpendicular to the longitudinal direction, and an X-axis direction is a width direction perpendicular to the longitudinal direction and to the lamination direction.

The gas sensor element 7 includes a rectangular-parallelepiped element body 70 extending in the longitudinal direction, and the porous protection layer 17 which covers a forward end portion (a lower end portion in FIG. 2) of the element body 70. The element body 70 is configured such that a plate-shaped element 71 extending in the longitudinal direction and a plate-shaped heater 73 extending in the longitudinal direction are laminated together (Refer to FIG. 3). The element body 70 has the detecting section 90 provided in its forward end region and adapted to detect a particular gas contained in gas to be measured. The protection layer 17 is formed of porous alumina and provided on a forward end surface 127 and side surfaces (the first main surface 21, the second main surface 23, a first side surface 111, and a second side surface 113) of the element body 70 in such a manner as to cover at least the detecting section 90.

Figure 3:
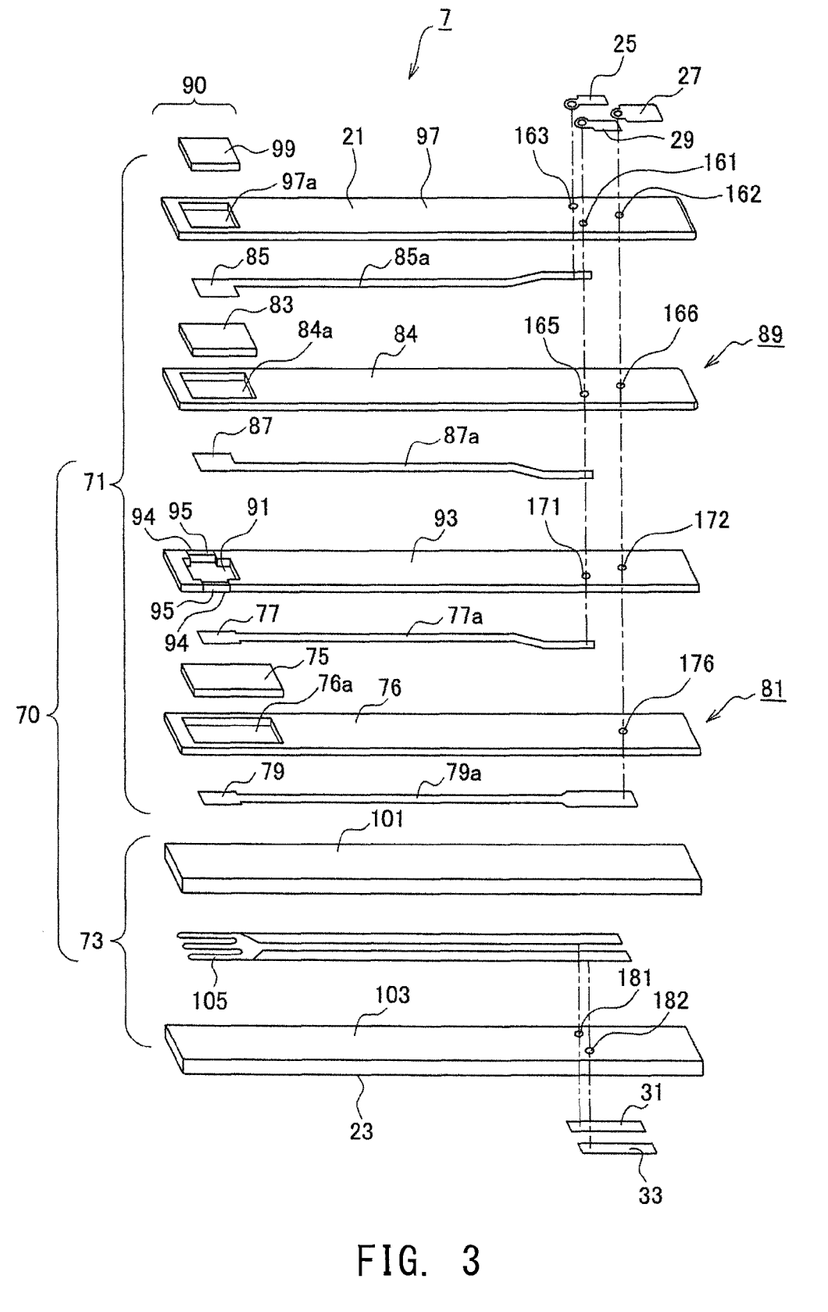
FIG. 3 is an exploded perspective view showing the gas sensor element.

FIG. 3 is an exploded perspective view showing the gas sensor element 7. FIG. 3 omits illustration of the protection layer 17.

As shown in FIG. 3 in an exploded condition, the element body 70 of the gas sensor element 7 includes the plate-shaped element 71 disposed on one side (upper side in FIG. 3) in the lamination direction and extending in the longitudinal direction, and the plate-shaped heater 73 disposed on a side (back side) opposite the element 71 and extending in the longitudinal direction.

The element 71 includes an oxygen concentration cell 81, an oxygen pump cell 89, an insulating spacer 93, and an insulating substrate 97.

The oxygen concentration cell 81 includes an insulating member 76, a solid electrolyte body 75, a porous electrode 77, a lead 77a, a porous electrode 79, and a lead 79a.

The insulating member 76 is a plate-shaped member formed primarily of alumina, and includes a through hole 76a extending therethrough in its thickness direction. The solid electrolyte body 75 is disposed within the through hole 76a of the insulating member 76. A pair of the porous electrodes 77 and 79 are disposed on the front and back surfaces of the solid electrolyte body 75, respectively, such that the solid electrolyte body 75 is sandwiched between the pair of porous electrodes.

That is, the oxygen concentration cell 81 is an embedded-type cell in which the solid electrolyte body 75 is embedded in the through hole 76a of the insulating member 76.

The lead 77a is connected to the porous electrode 77 at one end thereof, and disposed in such a manner as to extend in the longitudinal direction of the gas sensor element 7 (the element body 70) (in the horizontal direction in FIG. 3). The lead 79a is connected to the porous electrode 79 at one end thereof, and disposed in such a manner as to extend in the longitudinal direction of the gas sensor element 7 (the element body 70) (in the (horizontal direction in FIG. 3).

The oxygen pump cell 89 includes an insulating member 84, a solid electrolyte body 83, a porous electrode 85, a lead 85a, a porous electrode 87, and a lead 87a.

The insulating member 84 is a plate-shaped member formed primarily of alumina, and includes a through hole 84a extending therethrough in its thickness direction. The solid electrolyte body 83 is disposed within the through hole 84a of the insulating member 84. A pair of the porous electrodes 85 and 87 are disposed on the front and back surfaces of the solid electrolyte body 83, respectively, such that the solid electrolyte body 83 is sandwiched between the pair of porous electrodes.

That is, the oxygen pump cell 89 is an embedded-type cell in which the solid electrolyte body 83 is embedded in the through hole 84a of the insulating member 84.

The lead 85a is connected to the porous electrode 85 at one end thereof, and disposed in such a manner as to extend in the longitudinal direction of the gas sensor element 7 (the element body 70) (in the horizontal direction in FIG. 3). The lead 87a is connected to the porous electrode 87 at one end thereof, and disposed in such a manner as to extend in the longitudinal direction of the gas sensor element 7 (the element body 70) (in the horizontal direction in FIG. 3).

The solid electrolyte bodies 75 and 83 are formed of zirconia which contains yttria as a stabilizer in solid solution. In this configuration, the cross-section of the solid electrolyte body 75 along a plane perpendicular to a lamination direction has a greater cross-sectional area than that of solid electrolyte body 83.

The porous electrodes 77, 79, 85, and 87 and the leads 77a, 79a, 85a, and 87a are formed primarily of Pt.

The insulating spacer 93 is a plate-shaped member formed primarily of alumina, and includes a hollow gas measuring chamber 91 formed therein. The insulating spacer 93 is laminated between the oxygen concentration cell 81 and the oxygen pump cell 89. One of the porous electrodes 77 of the oxygen concentration cell 81 and one of the porous electrodes 87 of the oxygen pump cell 89 are disposed in such a manner as to be exposed to the hollow gas measuring chamber 91.

The element 71 has two gas inlets 94 formed in respective sides thereof (sides of the insulating spacer 93). The gas inlets 94 serve as openings for introducing exhaust gas (gas to be measured) and communicate with the gas measuring chamber 91. Diffusion controlling portions 95 are formed in respective paths extending from the two gas inlets 94 to the gas measuring chamber 91. The diffusion controlling portions 95 are porous bodies formed of, for example, alumina and control diffusion of gas to be measured which flows into the gas measuring chamber 91. The diffusion controlling portions 95 are partially exposed from the gas inlets 94.

That is, in the gas sensor element 7, the gas inlets 94 are formed in the outermost surfaces of the element body 70 and face in two different directions, and the diffusion controlling portions 95 are exposed in the two different directions.

An insulating substrate 97 is a plate-shaped member formed primarily of alumina, and includes a space portion 97a extending therethrough in its thickness direction. The insulating substrate 97 has a ventilating portion 99 embedded in the space portion 97a, and the ventilating portion 99 is a porous body similar to the case of the diffusion controlling portions 95. The ventilating portion 99 allows the porous electrode 85 of the oxygen pump cell 89 to be exposed to gas to be measured.

The gas measuring chamber 91 is located in a forward end region (in a left end region in FIG. 3) of the element body 70 (specifically, the element 71). With respect to the longitudinal direction of the element 71, a region where the gas measuring chamber 91 is formed, and a region located forward of the gas measuring chamber 91 constitute the detecting section 90 for detecting oxygen.

Meanwhile, the heater 73 is formed such that a heat generating resistor pattern 105 formed primarily of Pt is sandwiched between insulating substrates 101 and 103 formed primarily of alumina.

The gas sensor element 7 has the three electrode pads 25, 27, and 29 formed on a rear end portion (a right end portion in FIG. 3) of the first main surface 21, and the two electrode pads 31 and 33 formed on a rear end portion of the second main surface 23.

As shown in FIG. 3, the electrode pad 29 (the right-hand electrode pad in FIG. 2) formed on the first main surface 21 is electrically connected to the porous electrode 77 of the oxygen concentration cell 81 through a through hole 161 provided in the insulating substrate 97, a through hole 165 provided in the insulating member 84, a through hole 171 provided in the insulating spacer 93, and the lead 77a. The electrode pad 29 is also electrically connected to the porous electrode 87 of the oxygen pump cell 89, through the through hole 161 provided in the insulating substrate 97, the through hole 165 provided in the insulating member 84, and the lead 87a. Thus, the porous electrode 77 and the porous electrode 87 are electrically connected to each other and thus have the same electrical potential.

A conductor is disposed within each through hole (e.g. through hole 161 or 165). Examples of the configuration of the conductor disposed within a through hole include one in which a conductor is disposed along the inner wall surface of a through hole such that a hollow space remains along the center axis (the penetration direction) of the through hole, and another one in which a conductor fills a through hole.

Also, as shown in FIG. 3, an electrode pad 27 (a central electrode pad in FIG. 2) is electrically connected to the porous electrode 79 of the oxygen concentration cell 81 through a through hole 162 provided in the insulating substrate 97, a through hole 166 provided in the insulating member 84, a through hole 172 provided in the insulating spacer 93, a through hole 176 provided in the insulating member 76, and the lead 79a. Furthermore, as shown in FIG. 3, a further electrode pad 25 (a left-hand electrode pad in FIG. 2) is electrically connected to the porous electrode 85 of the oxygen pump cell 89 through a through hole 163 provided in the insulating substrate 97 and the lead 85a.

Also, as shown in FIG. 3, the electrode pads 31 and 33 are electrically connected to respective opposite ends of the heat generating resistor pattern 105 through through holes 181 and 182, respectively, provided in the insulating substrate 103.

Referring back to FIG. 2, since the thus-configured gas sensor element 7 is an elongated, substantially rectangular-parallelepiped plate member, it has four edges (longitudinal ridgelines) H1, H2, H3, and H4 extending its longitudinal direction (Y-axis direction in FIG. 2).

More specifically, the gas sensor element 7 has four outer walls extending its longitudinal direction; i.e., the first main surface 21 and the second main surface 23, and the first side surface 111 and the second side surface 113 in contact with the first main surface 21 and the second main surface 23. Also, the gas sensor element 7 has the first edge H1, which is a ridgeline between the first main surface 21 and the first side surface 111; the second edge H2, which is a ridgeline between the first main surface 21 and the second side surface 113; the third edge H3, which is a ridgeline between the second main surface 23 and the second side surface 113; and the fourth edge H4, which is a ridgeline between the second main surface 23 and the first side surface 111.

The gas sensor element 7 has a rear end surface 129 perpendicular to the longitudinal direction at its rear end (an upper end in FIG. 2).

1-3. Electrode Pads and Through Holes

Next, the electrode pads 25, 27, and 29 and through holes of the gas sensor element 7 will be described.

Figure 4:
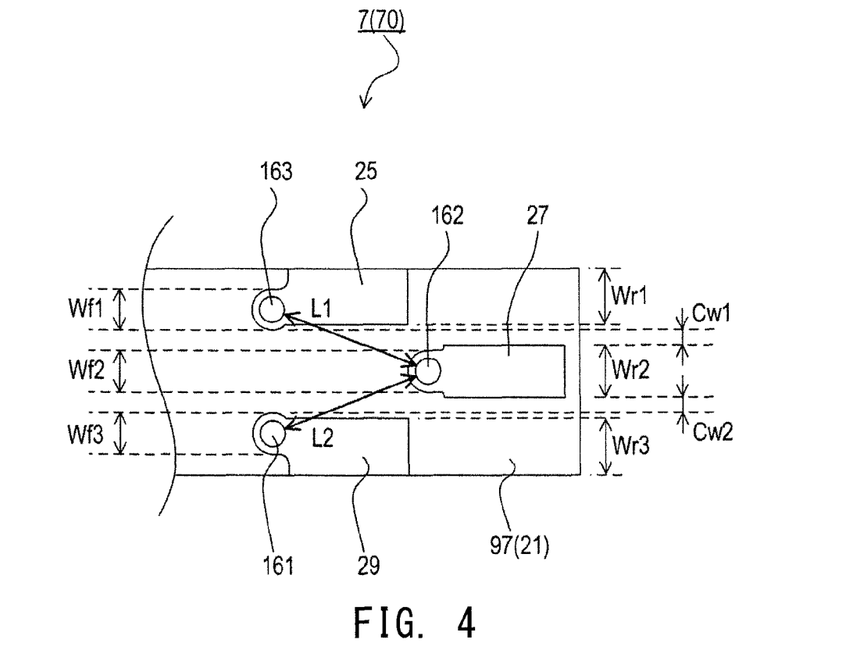
FIG. 4 is an explanatory view showing the layout of electrode pads in a rear end region of the gas sensor element.

FIG. 4 is an explanatory view showing the layout of the electrode pads 25, 27, and 29 in the rear end region of the gas sensor element 7.

The electrode pads 25, 27, and 29 are formed on the first main surface 21 of the gas sensor element 7 such that the electrode pads 25, 27, and 29 are connected to the through holes 163, 162, and 161 in their forward end regions (located on the left side in FIG. 4). That is, the plurality of through holes 163, 162, and 161 are formed in the insulating substrate 97 at positions within the forward end regions of the corresponding electrode pads 25, 27, and 29 to which the through holes are connected.

In the thus-configured gas sensor element 7, the through holes 163, 162, and 161 are formed within the forward end regions of the electrode pads 25, 27, and 29, rather than being formed within the longitudinal rear end regions and center regions of the electrode pads 25, 27, and 29. Since in each of the electrode pads 25, 27, and 29, the region of the electrode pad other than its forward end region (i.e. its rear end region and its center region) occupies a greater area than that of the forward end region, it is easy to bring the connection terminals 15 into contact with the regions of the electrode pads 25, 27, and 29 other than the forward end regions thereof.

Since it becomes easy to employ a configuration in which the connection terminals 15 are connected to the regions of the electrode pads 25, 27, and 29 other than their forward end regions as descried above, it is possible to restrain the connection terminals 15 from coming into contact with the through holes 163, 162, and 161, to thereby restrain occurrence of an electrical connection failure between the connection terminals 15 and the electrode pads 25, 27, and 29.

Moreover, in the thus-configured gas sensor element 7, the connection terminals 15 do not move over the through holes 163, 162, and 161 when the connection terminals 15 are moved (slid) on the outer surface of the gas sensor element 7 from the rear end side toward the forward end side thereof in a step of assembling the gas sensor element 7 and the connection terminals 15, which are to be connected to the electrode pads 25, 27, and 29. As a result, it is possible to restrain some of the connection terminals 15 from being caught by the through holes 163, 162, and 161 and deformed. Thus, it is possible to restrain occurrence of an electrical connection failure between the connection terminals 15 and the electrode pads 25, 27, and 29 (wire breakage anomaly) due to the deformation of the connection terminals 15.

The plurality of electrode pads 25, 27, and 29 of the gas sensor element 7 are disposed such that a gap in the width direction of the face (the first main surface 21) of the insulating substrate 97 (the vertical direction in FIG. 4) is formed between the electrode pads.

Specifically, the electrode pads 25 and 27 are disposed such that a widthwise gap Cw1 is formed between the electrode pads 25 and 27, and the electrode pads 27 and 29 are disposed such that a widthwise gap Cw2 is formed between the electrode pads 27 and 29.

Since the gas sensor element 7 has the above-described configuration, a short circuit anomaly in which a short circuit is formed between two of the electrode pads 25, 27 and 29 is less likely to occur. Specifically, when the connection terminals 15 are moved (slid) on the outer surface of the gas sensor element 7 from the rear end side toward the forward end side thereof in the step of assembling the gas sensor element 7 and the connection terminals 15, the electrode pads 25, 27 and 29 may be scraped by the connection terminals 15, and shavings of the electrode pads 25, 27 and 29 may be produced. Even in such a case, the above-mentioned short circuit anomaly is less likely to occur.

More specifically, when shavings of the electrode pads 25, 27, and 29 are produced, the shavings move mainly in the longitudinal direction of the first main surface 21 of the insulating substrate 97 which is the direction in which the connection terminals 15 move (in the horizontal direction in FIG. 4), and the range of the movement of the shavings in the width direction of the first main surface 21 of the insulating substrate 97 (in the vertical direction in FIG. 4) is small. Moreover, since the plurality of electrode pads 25, 27, and 29 are disposed such that a widthwise gap is formed between the electrode pads, electrical continuity between the electrode pads due to shavings becomes less likely to occur, and thus an electrical connection failure (short-circuit anomaly) due to electrical continuity between the electrode pads 25, 27, and 29 becomes less likely to occur.

Each of the electrode pads 25, 27, and 29 has a rear end region and a forward end region located rearward and forward of the center point of the corresponding through hole 163, 162, or 161, and is shaped such that the maximum width Wr1, Wr2, or Wr3 of the rear end region is greater than the maximum width Wf1, Wf2, or Wf3 of the forward end region.

This means that, since the respective rear end regions of the electrode pads 25, 27, and 29 located rearward of the center points of the corresponding through holes 163, 162, and 161 serve as contact regions for contact with the connection terminals 15, the electrode pads 25, 27, and 29 whose rear end regions have larger maximum widths Wr1, Wr2, and Wr3 can achieve good electrical contact with the connection terminals 15.

In the gas sensor element 7, the distance between any adjacent two of the plurality of through holes 163, 162, and 161 is 2.3 [mm] or less. Specifically, the distance L1 between the through holes 163 and 162 is 2.3 [mm] and the distance L2 between the through holes 162 and 161 is 2.3 [mm].

Figure 5:
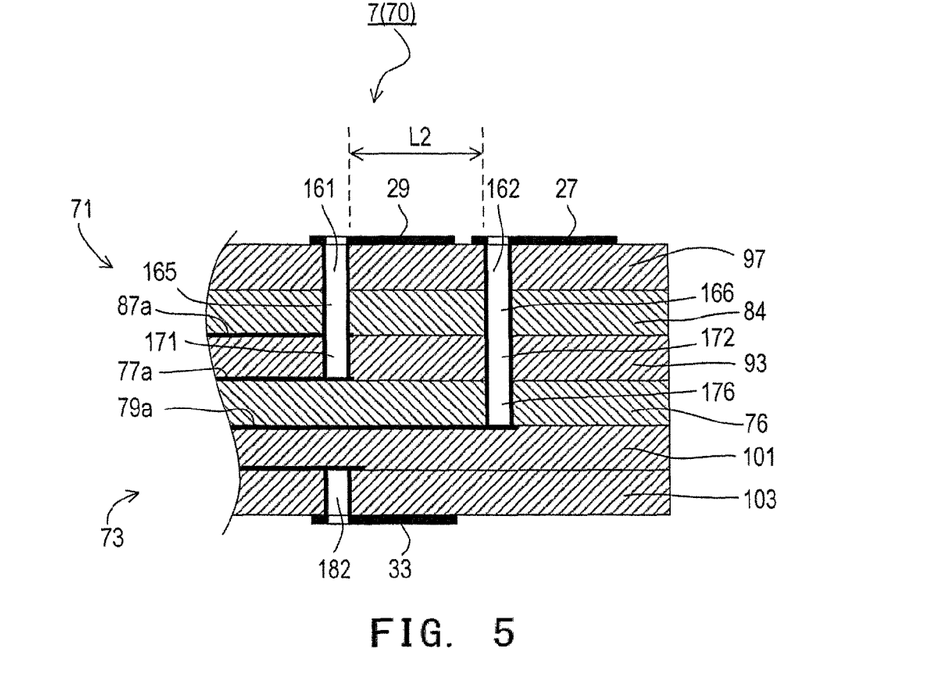
FIG. 5 is an enlarged cross sectional view showing the internal configuration of the gas sensor element in a through hole forming region.

FIG. 5 is an enlarged cross sectional view showing the internal configuration of the gas sensor element 7 in the through hole forming region thereof.

Since the plurality of through holes 163, 162, and 161 are arranged such that the distance between any adjacent two of the plurality of through holes 163, 162, and 161 is 2.3 [mm] or less, the region where the through holes 163, 162, and 161 are formed can be reduced in size, and the gas sensor element 7 can be reduced in size.

Since the oxygen concentration cell 81 and the oxygen pump cell 89 of the gas sensor element 7 are embedded-type cells, the through holes of the cells can be formed in the insulating members 76 and 84, rather than in the solid electrolyte bodies. As a result, even when the distance between the plurality of through holes 165 and 166 is rendered less than 4.8 [mm], occurrence of leak current (leakage current) between the plurality of through holes 165 and 166 through the solid electrolyte bodies 83 and 75 can be restrained.

1-4. Method of Manufacturing Gas Sensor

A method of manufacturing the air/fuel ratio sensor 1 of the present embodiment will be described with reference to FIGS. 6 and 7.

Figure 6:
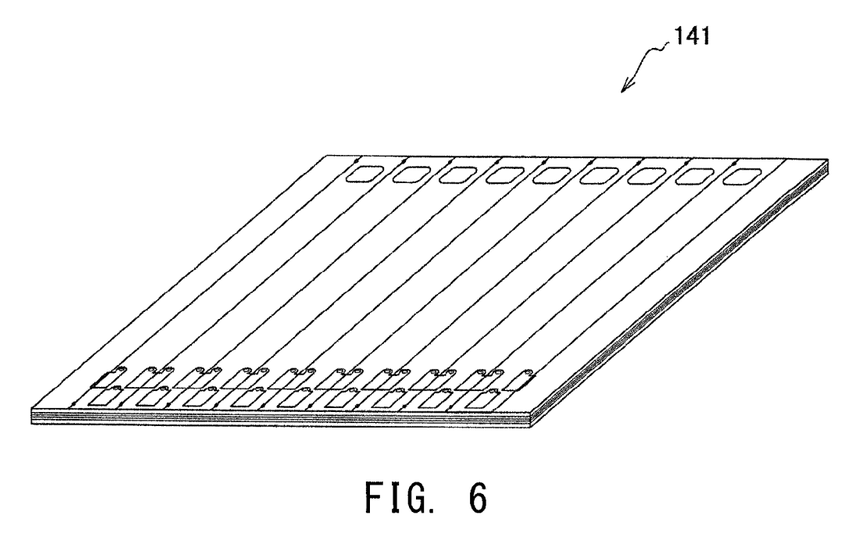
FIG. 6 is an explanatory view regarding a method of manufacturing green compacts of the gas sensor elements.

FIG. 6 is an explanatory view regarding a method of manufacturing a green compact 141 of the gas sensor elements. FIG. 7 is an explanatory view showing the gas sensor element in the middle of manufacture.

In manufacture of the gas sensor element 7, first, an uncompressed laminate is prepared by laminating together publicly known various materials used to form the gas sensor element 7; specifically, green solid electrolyte sheets used to form the solid electrolyte bodies 75 and 83 of the element 71, green insulating sheets used to form the insulating member 76, the insulating member 84, and the insulating substrate 97 of the element 71, green insulating sheets used to form the insulating substrates 101 and 103 of the heater 73, among others. The uncompressed laminate has green electrode pads which are to become the electrode pads 25, 27, 29, 31, and 33, among others, formed beforehand therein.

Among these materials, for example, the green solid electrolyte sheet is formed in the following manner. First, alumina powder, butyral resin, etc., are added to ceramic powder which predominantly contains zirconia. Into the resultant mixture, a mixed solvent (toluene and methyl ethyl ketone) is mixed, thereby forming slurry. The slurry is formed into a sheet by a doctor blade process, and the mixed solvent is volatilized, thereby yielding the green solid electrolyte sheet.

Also, the green insulating sheet is formed in the following manner. First, butyral resin and dibutyl phthalate are added to ceramic powder which predominantly contains alumina. Into the resultant mixture, a mixed solvent (toluene and methyl ethyl ketone) is mixed, thereby forming slurry. The slurry is formed into a sheet by the doctor blade process, and the mixed solvent is volatilized, thereby yielding the green insulating sheet.

Furthermore, green diffusion controlling portions are formed in the following manner. First, 100 mass % alumina powder, a material to be burnt away by heating (e.g. carbon), and a plasticizer are wet-mixed, thereby forming slurry in which the alumina powder and the plasticizer are dispersed. The plasticizer contains butyral resin and DBP. The slurry is applied to regions where the diffusion controlling portions 95 and the ventilating portion 99 are to be formed through firing, thereby forming the green diffusion controlling portions.

Then, the uncompressed laminate is compressed under a pressure of 1 MPa, thereby yielding the green compact 141 as shown in FIG. 6. A method of manufacturing the uncompressed laminate is similar to a publicly known method of manufacturing a gas sensor element; therefore, detailed description of the method is omitted.

The green compact 141 yielded through application of pressure is cut into a plurality of (e.g., ten) green laminates, each having a predetermined size substantially identical to that of the element 71 and the heater 73 of the gas sensor element 7.

Figure 7:
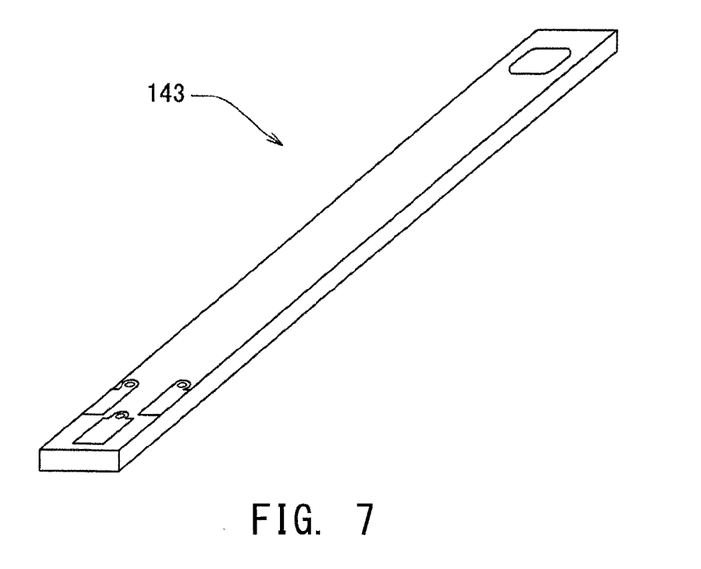
FIG. 7 is an explanatory view showing the gas sensor element in the middle of manufacture.

Subsequently, the green laminate is debindered and is, furthermore, subjected to regular firing at 1,500° C. for one hour, thereby yielding a fired laminate 143 as shown in FIG. 7. The fired laminate 143 corresponds to the element body 70.

After the element body 70 is yielded as mentioned above, a green protection layer is formed around a forward end portion of the element body 70. The green protection layer becomes the protection layer 17 (see FIG. 2) through firing.

Subsequently, heat treatment is performed on the green protection layer. Specifically, the element body 70 on which the green protection layer is formed is subjected to heat treatment at 1,000° C. for three hours, thereby yielding the gas sensor element 7 with the protection layer 17 formed thereon.

The thus-formed gas sensor element 7 is assembled to the metallic shell 5 in an assembling step.

Specifically, in this assembling step, the gas sensor element 7 manufactured by the above method is inserted into the metallic holder 51; furthermore, the gas sensor element 7 is fixed in place by the ceramic holder 41 and the talc ring 43, thereby forming a subassembly. Subsequently, while the subassembly is fixed to the metallic shell 5, and a portion of the gas sensor element 7 on the rear end side in the direction of the axial line 0 is inserted through the talc ring 45 and the ceramic sleeve 9, these members are inserted into the metallic shell 5.

Then, the rear end portion 47 of the metallic shell 5 is crimped to the ceramic sleeve 9, thereby yielding a lower subassembly. The protector 55 is attached beforehand to the lower subassembly.

Meanwhile, the outer tube 57, the separator 13, the grommet 61, etc., are assembled together, thereby yielding an upper subassembly. Then, the lower subassembly and the upper subassembly are joined together, thereby yielding the air/fuel ratio sensor 1.

1-5. Test for Measuring Insulation Resistance Between Through Holes

A measurement test which was carried out so as to measure the insulation resistance between the through holes of the gas sensor element 7 of the present invention will be described below.

In this test, after the rear end portion of the gas sensor element 7 (the region where the electrode pads 25, 27, and 29 are formed) was heated, the inter-through-hole insulation resistance was measured for all possible pairs of through holes out of the three through holes 161, 162, and 163. Specifically, three insulation resistances; i.e., the insulation resistance "between the through holes 161 and 163," the insulation resistance "between the through holes 163 and 162," and the insulation resistance "between the through holes 162 and 161" were measured.

In this test, two samples of gas sensor elements (first and second samples) were used. The distance "between the through holes 161 and 163" was 1.2 [mm], the distance "between the through holes 163 and 162" was 2.3 [mm], and the distance "between the through holes 162 and 161" was 2.3 [mm].

Figure 8:
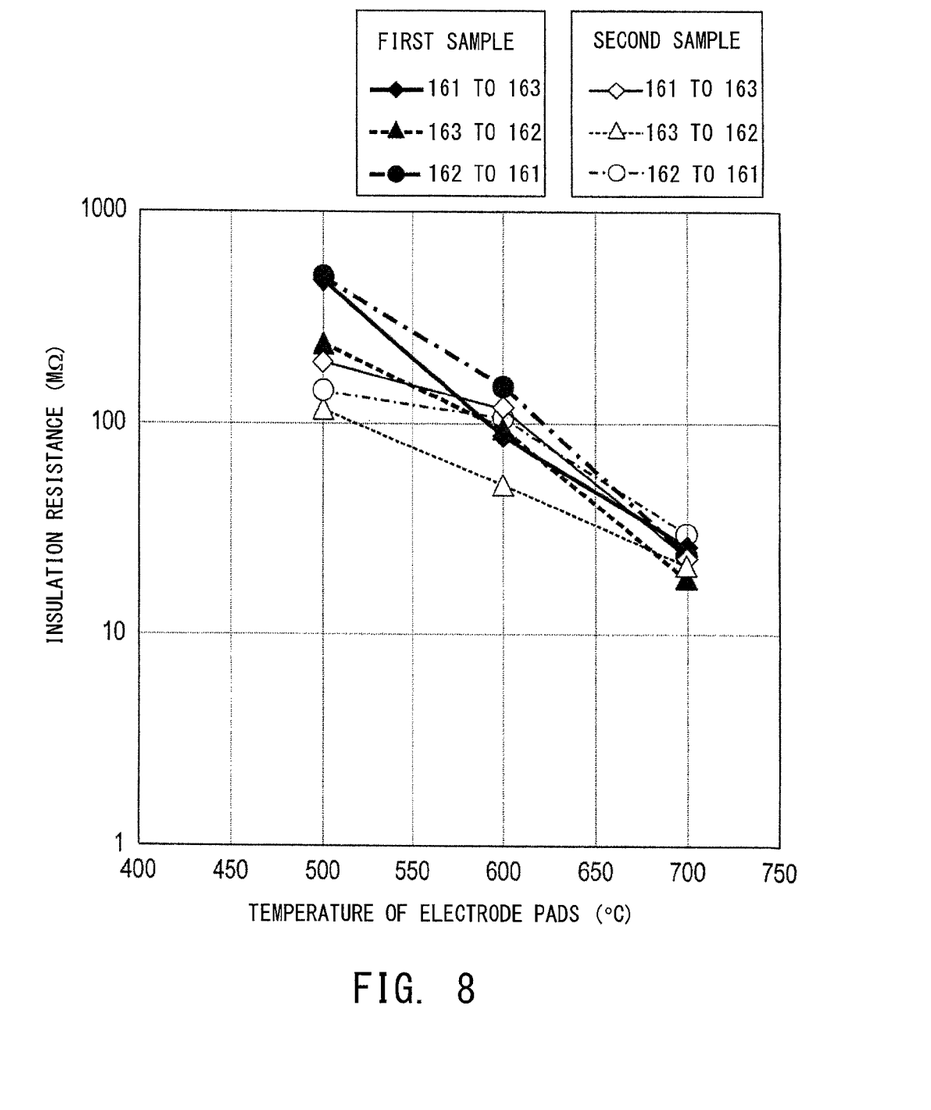
FIG. 8 shows test results of a resistance measurement test for measuring insulation resistances between the through holes.

FIG. 8 shows the results of the test performed so as to measure the insulation resistances between the through holes.

According to the test results, in the first and second samples, all the insulation resistance "between the through holes 161 and 163", the insulation resistance "between the through holes 163 and 162", and the insulation resistance "between the through holes 162 and 161" were 10 [MΩ] or higher over the entire temperature range (500 to 700 [° C.]). In particular, at 500° C., all the measured insulation resistances were 100 [MΩ] or higher.

In a conventional gas sensor element having through holes formed in a solid electrolyte body, in order to restrict occurrence of leak current (leakage current) between the through holes, the distance between any adjacent two of the through holes is set to 4.8 [mm] or greater so that the inter-through-hole insulation resistance becomes 1.0 [MΩ] or higher.

Though the gas sensor element of the present invention is configured such that the distance between the through holes is less than that of the conventional gas sensor element, the inter-through-hole insulation resistance becomes 10 [MΩ] or higher.

Thus, in the case of the gas sensor element of the present invention, the inter-through-hole distance can be made smaller compared with the conventional gas sensor element having through holes formed in the solid electrolyte body thereof.

1-6. Effects

As described above, the gas sensor element 7 in the air/fuel ratio sensor 1 of the present embodiment includes the electrode pads 25, 27, and 29 formed such that the electrode pads 25, 27, and 29 are connected to the through holes 163, 162, and 161 in their respective forward end regions. That is, the plurality of through holes 163, 162, and 161 are formed in the insulating substrate 97 at positions within the forward end regions of the electrode pads 25, 27, 29 to which the through holes 163, 162, and 161 are connected.

In the thus-configured gas sensor element 7, the through holes 163, 162, and 161 are formed within the forward end regions of the electrode pads 25, 27, and 29, rather than being formed within the longitudinal rear end regions and center regions of the electrode pads 25, 27, and 29. Since in each of the electrode pads 25, 27, and 29, the region of the electrode pad other than its forward end region (i.e. its rear end region and its center region) occupies a greater area than that of the forward end region, it is easy to bring the connection terminals 15 into contact with the regions of the electrode pads 25, 27, and 29 other than the forward end regions thereof.

Since it becomes easy to employ a configuration in which the connection terminals 15 are connected to the regions of the electrode pads 25, 27, and 29 other than their forward end regions as descried above, it is possible to restrain the connection terminals 15 from coming into contact with the through holes 163, 162, and 161, to thereby restrain occurrence of an electrical connection failure between the connection terminals 15 and the electrode pads 25, 27, and 29.

Moreover, in the thus-configured gas sensor element 7, the connection terminals 15 do not move over the through holes 163, 162, and 161 when the connection terminals 15 are moved (slid) on the outer surface of the gas sensor element 7 from the rear end side toward the forward end side thereof in the step of assembling the gas sensor element 7 and the connection terminals 15, which are to be connected to the electrode pads 25, 27, and 29.

As a result, it is possible to restrain some of the connection terminals 15 from being caught by the through holes 163, 162, and 161 and deformed. Thus, it is possible to restrain occurrence of an electrical connection failure between the connection terminals 15 and the electrode pads 25, 27, and 29 (wire breakage anomaly) due to the deformation of the connection terminals 15.

Therefore, the air/fuel ratio sensor 1 including the gas sensor element 7 can restrain occurrence of an electrical connection failure between the electrode pads 25, 27, and 29 and the connection terminals 15. Also, the air/fuel ratio sensor 1 including the gas sensor element 7 can restrain occurrence of anomaly in the signal paths for sensor signals led to the connection terminals 15.

Moreover, the configuration in which the through hole 162 is formed within the forward end region of the electrode pad 27 can decrease the length of lead 79$a$ of the oxygen concentration cell 81 compared to the configuration in which the through hole 162 is formed within the rear end region of the electrode pad 27. Therefore, the former configuration reduces the amount of noble metal used for the lead 79$a$, thereby reducing the material costs of the gas sensor element 7 and thus reducing manufacturing costs of the gas sensor 7.

In the gas sensor element 7, the electrode pads 25 and 27 are disposed such that the gap Cw1 in the width direction of the face (the first main surface 21) of the insulating substrate 97 is formed between the electrode pads 25 and 27, and the electrode pads 27 and 29 are disposed such that the gap Cw2 in the width direction of the face (the first main surface 21) of the insulating substrate 97 is formed between the electrode pads 27 and 29.

Since the gas sensor element 7 has the above-described configuration, a short circuit anomaly in which a short circuit is formed between two of the electrode pads 25, 27 and 29 is less likely to occur. Specifically, when the connection terminals 15 are moved (slid) on the outer surface of the gas sensor element 7 from the rear end side toward the forward end side thereof in the step of assembling the gas sensor element 7 and the connection terminals 15, the electrode pads 25, 27 and 29 may be scraped by the connection terminals 15, and shavings of the electrode pads 25, 27 and 29 may be produced. Even in such a case, the above-mentioned short circuit anomaly is less likely to occur.

More specifically, when shavings of the electrode pads 25, 27, and 29 are produced, the shavings move mainly in the longitudinal direction of the first main surface 21 of the insulating substrate 97 which is the direction in which the connection terminals 15 move (in the horizontal direction in FIG. 4), and the range of the movement of the shavings in the width direction of the first main surface 21 of the insulating substrate 97 (in the vertical direction in FIG. 4) is small. Moreover, since the plurality of electrode pads 25, 27, and 29 are disposed such that a widthwise gap is formed between the electrode pads, electrical continuity between the electrode pads due to shavings becomes less likely to occur, and thus an electrical connection failure (short-circuit anomaly) due to electrical continuity between the electrode pads 25, 27, and 29 becomes less likely to occur.

Therefore, the gas sensor element 7 can restrain occurrence of an electrical connection failure between the electrode pads 25, 27, and 29 and the connection terminals 15.

Each of the electrode pads 25, 27, and 29 has a rear end region and a forward end region located rearward and forward of the center point of the corresponding through hole 163, 162, or 161, and is shaped such that the maximum width Wr1, Wr2, or Wr3 of the rear end region is greater than the maximum width Wf1, Wf2, or Wf3 of the forward end region.

Since the respective rear end regions of the electrode pads 25, 27, and 29 located rearward of the center points of the corresponding through holes 163, 162, and 161 serve as contact regions for contact with the connection terminals 15, the electrode pads 25, 27, and 29 whose rear end regions have larger maximum widths Wr1, Wr2, and Wr3 can achieve good electrical contact with the connection terminals 15.

Therefore, the gas sensor element 7 can restrain occurrence of an electrical connection failure between the electrode pads 25, 27, and 29 and the connection terminals 15, and can restrain occurrence of anomaly in the signal paths for sensor signals led to the connection terminals 15.

In the gas sensor element 7, the distance between any adjacent two of the plurality of through holes is 2.3 [mm].

When the plurality of through holes are arranged in the above-described manner, the region where the through holes are formed can be reduced in size, and the gas sensor element can be reduced in size.

As apparent from the above-mentioned test results shown in FIG. 8, even when the distance between the plurality of through holes is set in the above-described manner, occurrence of leak current (leakage current) between the plurality of through holes can be restrained.

Therefore, the gas sensor element 7 can restrain occurrence of leak current (leakage current) between the plurality of through holes, and can restrain occurrence of anomaly in the signal paths for sensor signals led to the connection terminals 15.

The air/fuel ratio sensor 1 including the gas sensor element 7 can restrain occurrence of an electrical connection failure between the electrode pads 25, 27, and 29 and the connection terminals 15, and can restrain occurrence of anomaly in the signal paths for sensor signals led from the electrode pads of the gas detection element to the connection terminals 15.

1-7. Correspondence Between Claims and Present Embodiment

Correspondence in wording between claims and the present embodiment will be described below.

The air/fuel ratio sensor 1 corresponds to an example of the gas sensor. The oxygen concentration cell 81 and oxygen pump cell 89 correspond to an example of the cell (embedded-type cell). The insulating substrate 97 corresponds to an example of the insulating substrate. The electrode pads 25, 27, and 29 correspond to an example of the plurality of electrode pads. The through holes 165, 166, and 176 correspond to an example of the first through holes, and the through holes 161, 162, and 163 correspond to an example of the second through holes.

The through hole 76a corresponds to an example of the hollow space, and the insulating member 76 corresponds to an example of the frame member. The through hole 84a corresponds to an example of the hollow space and the insulating member 84 corresponds to an example of the frame member.

The porous electrodes 77 and 79 correspond to an example of the pair of electrodes, and the porous electrodes 85, 87 correspond to an example of the pair of electrodes. The leads 77a and 79a correspond to an example of the pair of leads, and the leads 85a and 87a correspond to an example of the pair of leads.

2. Other Embodiments

In the above, an embodiment of the present invention has been described; however, the present invention is not limited to the embodiment and may be embodied in various other forms without departing from the gist of the invention.

For example, the layout of the electrode pads 25 and 29 and the electrode pad 27 is not limited to that in the above-described embodiment in which the electrode pads 25 and 29 and the electrode pad 27 are disposed such that no gap in the longitudinal direction of the face (the first main surface 21) of the insulating substrate 97 is formed between the electrode pads 25 and 29 and the electrode pad 27.

Figure 9:
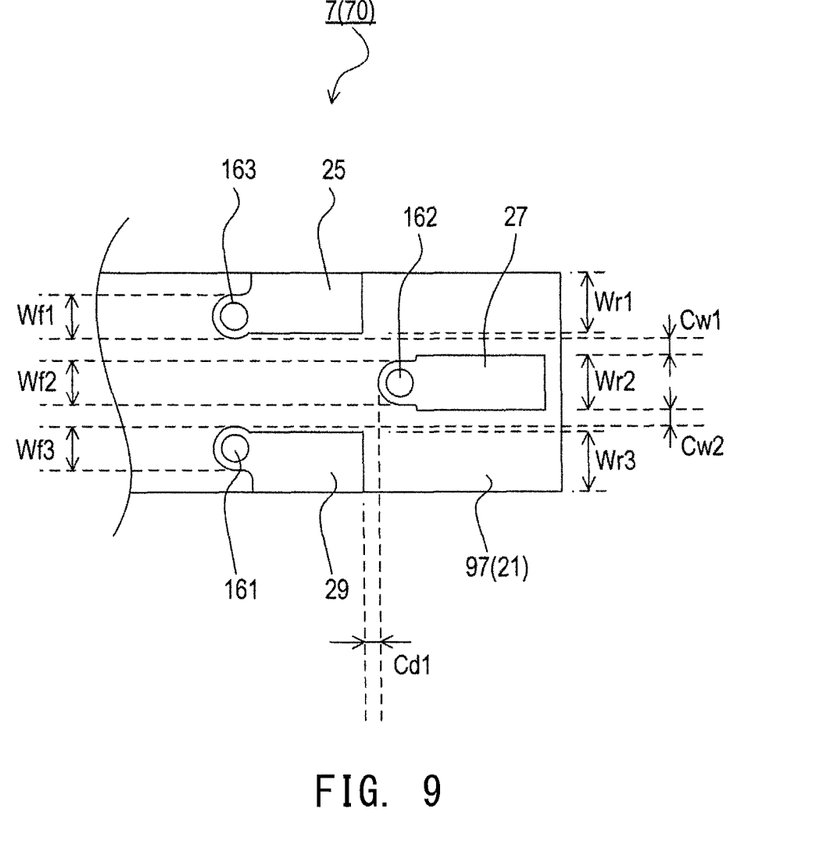
FIG. 9 is an explanatory view showing the layout of electrode pads in the rear end region of a gas sensor element according to a second embodiment of the present invention.

Specifically, as in the case of a gas sensor element of a second embodiment shown in FIG. 9, the electrode pads 25 and 29 and the electrode pad 27 may be disposed such that a gap Cd1 in the longitudinal direction of the face (the first main surface 21) of the insulating substrate 97 is formed between the electrode pads 25 and 29 and the electrode pad 27.

As a result of the electrode pads 25 and 29 and the electrode pad 27 being disposed such that the lengthwise gap Cd1 is formed between the electrode pads 25 and 29 and the electrode pad 27, long distances can be secured between the electrode pad 25 and electrode pad 27 and between the electrode pad 29 and electrode pad 27. Thus, the plurality of electrode pads 25, 27, and 29 are disposed apart from one another by a sufficient distance. Therefore, an electrical connection failure (short-circuit anomaly) due to electrical continuity between the electrode pads 25, 27, and 29 caused by any foreign matter becomes less likely to occur.

In the case where the plurality of electrode pads 25, 27, and 29 are disposed such that the widthwise gaps Cw1 and Cw2 are formed between the electrode pads and the lengthwise gap Cd1 is also formed between the electrode pads, the plurality of electrode pads 25, 27, and 29 are spaced from one another by a greater distance. Therefore, an electrical connection failure (short-circuit anomaly) due to electrical continuity between the electrode pads 25, 27, and 29 becomes more unlikely to occur.

Therefore, in a gas sensor including the thus-configured gas sensor element, an electrical connection failure (short-circuit anomaly) due to electrical continuity between the plurality of electrode pads 25, 27, and 29 becomes less likely to occur.

As to the layout of the electrode pads 25, 27, and 29, the electrode pads 25, 27, and 29 may disposed such that they overlap one another in the longitudinal direction of the face (the first main surface 21) of the insulating substrate 97. Specifically, as in the case of a gas sensor element of a third embodiment shown in FIG. 10, the electrode pads 25 and 29 and the electrode pad 27 may be disposed such that the electrode pads 25 and 29 overlap the electrode pad 27 in the longitudinal direction of the face (the first main surface 21) of the insulating substrate 97.

Figure 10:
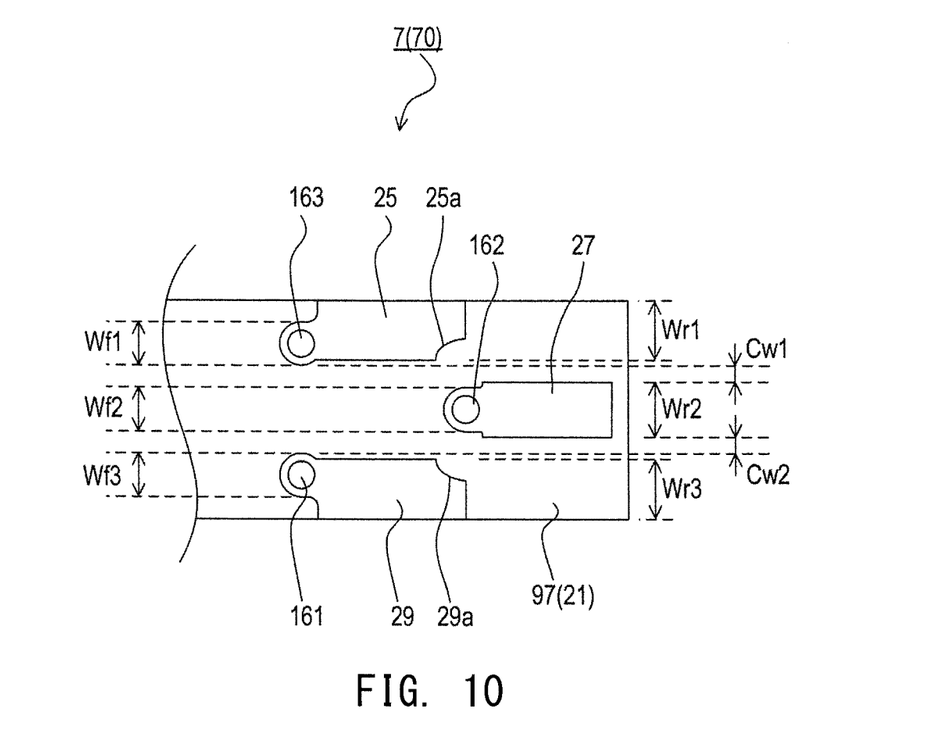
FIG. 10 is an explanatory view showing the layout of electrode pads in the rear end region of a gas sensor element according to a third embodiment of the present invention.

In such a case, the electrode pads 25 and 29 may be shaped to have respective cutouts 25a and 29a in their rear end regions. As a result, longer distances can be secured between the electrode pad 25 and the electrode pad 27 and between the electrode pad 29 and the electrode pad 27, whereby occurrence of leakage current (leak current) between the electrode pads can be restrained.

Therefore, in a gas sensor including the thus-configured gas sensor element, an electrical connection failure (short-circuit anomaly) due to electrical continuity between the plurality of electrode pads 25, 27, 29 becomes less likely to occur.

DESCRIPTION OF REFERENCE NUMERALS

1: air/fuel ratio sensor; 5: metallic shell; 7: gas sensor element; 15: connection terminal; 25: electrode pad; 25a: cutout; 27: electrode pad; 29: electrode pad; 29a: cutout; 75: solid electrolyte body; 76: insulating member; 76a: through hole; 77: porous electrode; 77a: lead; 79: porous electrode; 79a: lead; 81: oxygen concentration cell; 83: solid electrolyte body; 84: insulating member; 84a: through hole; 85: porous electrode; 85a: lead; 87: porous electrode; 87a: lead; 89: oxygen pump cell; 97: insulating substrate; 161: through hole; 162: through hole; 163: through hole; 165: through hole; 166: through hole; 171: through hole; 172: through hole; and 176: through hole

The invention claimed is:
1. A gas sensor for detecting a particular gas contained in gas to be measured comprising:
  a gas sensor element including;
    a cell having a frame member, a solid electrolyte body, a pair of electrodes, and a pair of leads, the frame member being formed of a plate-shaped insulating material extending in a longitudinal direction of the gas sensor element and having a hollow space in a forward end region thereof and a plurality of first through holes in a rear end region thereof which extend through the frame member in a thickness direction thereof and each of which has a conductor disposed therein, the solid electrolyte body being disposed within the hollow space, the pair of electrodes being formed on an outer surface of the solid electrolyte body, and the pair of leads being connected to the electrodes and the first through holes and extending in the longitudinal direction,
    an insulating substrate which is formed of a plate-shaped insulating material laminated on the cell and which has in a rear end region thereof a plurality of second through holes which extend therethrough in the thickness direction, each of which has a conductor disposed therein, and which communicate with the plurality of the first through holes, and
    a plurality of electrode pads disposed on an outer surface of the insulating substrate and connected to the plurality of second through holes;
  a plurality of connection terminals connected to the electrode pads; and a metallic shell for holding the gas sensor element in a state in which the connection terminals are connected to the electrode pads, wherein all of the plurality of second through holes are formed in the insulating substrate at positions within forward end regions of the corresponding electrode pads to which the second through holes are connected.

2. The gas sensor according to claim 1, wherein the plurality of electrode pads are disposed such that a gap in a width direction of a face of the insulating substrate is formed between the plurality of electrode pads.

3. The gas sensor according to claim 1, wherein the plurality of electrode pads are disposed such that a gap in a longitudinal direction of a face of the insulating substrate is formed between the plurality of electrode pads.

4. The gas sensor according to claim 1, wherein a distance between any adjacent two of the first through holes is 2.3 mm or less.

5. The gas sensor according to claim 1, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

6. The gas sensor according to claim 2, wherein the plurality of electrode pads are disposed such that a gap in a longitudinal direction of a face of the insulating substrate is formed between the plurality of electrode pads.

7. The gas sensor according to claim 2, wherein a distance between any adjacent two of the first through holes is 2.3 mm or less.

8. The gas sensor according to claim 3, wherein a distance between any adjacent two of the first through holes is 2.3 mm or less.

9. The gas sensor according to claim 6, wherein a distance between any adjacent two of the first through holes is 2.3 mm or less.

10. The gas sensor according to claim 2, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

11. The gas sensor according to claim 3, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

12. The gas sensor according to claim 4, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

13. The gas sensor according to claim 6, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

14. The gas sensor according to claim 7, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

15. The gas sensor according to claim 8, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

16. The gas sensor according to claim 9, wherein each of the electrode pads has a shape determined such that the maximum width of a rear end region of the electrode pad located rearward of a center point of the corresponding second through hole is greater than the maximum width of a forward end region of the electrode pad located forward of the center point of the corresponding second through hole.

17. The gas sensor according to claim 1, wherein a rear side region of each of the electrode pads is configured to be substantially larger than the forward end region of each of the electrode pads.

18. The gas sensor according to claim 17, wherein the rear side region is composed of a center region and a rear end region.

* * * * *